United States Patent [19]

Halloran

[11] Patent Number: 5,160,449
[45] Date of Patent: Nov. 3, 1992

[54] SHAMPOO SUSPENSION CONTAINING AMINE FUNCTIONAL POLYDIORGANOSILOXANE

[75] Inventor: Daniel J. Halloran, Midland, Mich.

[73] Assignee: Dow Corning Corporation, Midland, Mich.

[21] Appl. No.: 430,750

[22] Filed: Nov. 2, 1989

[51] Int. Cl.$^5$ .......................... C11D 3/30; A61K 7/09
[52] U.S. Cl. .......................... 252/174.15; 252/547; 252/DIG. 2; 252/DIG. 13; 252/DIG. 14; 424/70
[58] Field of Search .......................... 424/70; 252/174.15, 252/135, DIG. 2, DIG. 13, DIG. 14, 547

[56] References Cited

U.S. PATENT DOCUMENTS

| | | | |
|---|---|---|---|
| 3,957,970 | 5/1976 | Korkis | 252/174.15 |
| 3,964,500 | 6/1976 | Drakoff | 252/174.15 |
| 4,419,260 | 12/1983 | Reuter et al. | 252/174.15 |
| 4,559,227 | 12/1985 | Chandra et al. | 424/70 |
| 4,788,006 | 11/1988 | Bolich, Jr. et al. | 252/174.15 |

FOREIGN PATENT DOCUMENTS 0174097 8/1985 European Pat. Off. .

Primary Examiner—Prince Willis, Jr.
Assistant Examiner—J. Silbermann
Attorney, Agent, or Firm—Jim L. DeCesare

[57] ABSTRACT

A shampoo which is a mixture in the form of a suspension. The suspension includes at least one nonionic surfactant, at least one detersive surfactant, water, and an amine functional siloxane polymer. The shampoo suspension is free of viscosity modifying thickening compositions. The amine functional siloxane polymer is present in the suspension in the form of insoluble particles dispersed in the mixture, and the particles have a diameter in the suspension of the order of magnitude of between about one micron to about one hundred microns. The amine functional siloxane polymer should also have a mole percent of amine units of the order of magnitude of about 0.05 to about 1.5.

10 Claims, No Drawings

SHAMPOO SUSPENSION CONTAINING AMINE FUNCTIONAL POLYDIORGANOSILOXANE

BACKGROUND OF THE INVENTION

This invention relates to a shampoo suspension containing an amine functional siloxane polymer. More particularly, the invention is directed to a suspension for washing and conditioning hair, and in which the suspension is in the form of a mixture containing the polymer, water, a nonionic surfactant, and a detersive surfactant.

In U.S. Pat. No. 4,559,227, issued Dec. 17, 1985, there is disclosed and described in detail a shampoo formulation containing certain amine functional siloxane polymers, a nonionic surfactant, a detersive surfactant, and water. The shampoo in the '227 patent is in the form of a solution, and the term "solution" is described as meaning that the essential components are homogeneously mixed and that the components are subdivided to such an extent that there is no appearance of light scattering visible to the naked eye when a one inch diameter bottle of the mixture is viewed in sunlight. The solution in the '227 patent is also stated to preferably contain a thickener for the purpose of modifying the viscosity of the solution.

The present invention is an improvement in the shampoo formulation of the '227 patent, and is directed to a hair washing and conditioning composition in the form of a suspension, rather than in the form of a solution as described in the '227 patent. Like the '227 patent, the suspension of the present invention also contains an amine functional siloxane polymer, a nonionic surfactant, a detersive surfactant, and water, and therefore, for purposes of the present invention, the '227 patent is considered incorporated herein by reference.

The suspension form of the composition of the present invention possesses advantages beyond the solution form of the composition of the '227 patent. For instance, a suspension exists in a different state from that inherent in a solution form of composition, which will be described in more detail hereinafter. Secondly, because of the use in the present invention of a suspension instead of a solution as in the '227 patent, viscosity modifying thickening compositions are not required in order to formulate the hair washing and conditioning shampoos of the present invention. Hence, the suspension shampoo composition of the present invention is free of viscosity modifying ingredients such as thickening compositions, and goes beyond the disclosure of the '227 patent, and performs functions that differ substantially from that set forth in the prior art.

Several other significant differences exist between the suspension form of the shampoo formulation of the present invention and the solution form of the shampoo formulation of the '227 patent. For instance, the solution of the '227 patent contains soluble particles of the amine functional siloxane polymer, whereas the suspension of the present invention contains insoluble particles of the polymer. The order of magnitude of the soluble particles of the amine functional siloxane polymer of the '227 patent is about 0.03–0.04 microns and less in diameter, whereas the order of magnitude of the insoluble particles of the polymer in the suspension of the present invention is from one to about one hundred microns in diameter, with about ten microns being an average diameter. Thus, the particle size of the insoluble particles of the amine functional siloxane polymer in the suspension of the present invention is from twenty-five to twenty-five hundred times larger than the size of the particles of the soluble polymer in the solution of the '227 patent.

There is also a significant difference in the mole percent of amine units of the amine functional siloxane polymer of the '227 patent and the polymer of the present invention. In the '227 patent, the mole percent of amine units is said to be between two and five. In the present invention, the mole percent of amine units is much less, and can be as low as 0.05–0.8. Finally, there is a significant difference in the viscosity of the amine functional siloxane polymer of the '227 patent and the polymer of the present invention. In the '227 patent, the viscosity is generally less than about five hundred centistokes measured at twenty-five degrees Centigrade. In the present invention, the viscosity is much larger, and can be in excess of about one thousand centistokes measured at twenty-five degrees Centigrade, and can even be as high as thirteen thousand centistokes or more. Thus, the shampoo suspension of the present invention is significantly different from the solution type of shampoo described in the '227 patent.

SUMMARY OF THE INVENTION

This invention is directed to a shampoo which is a mixture in the form of a suspension. The suspension includes at least one nonionic surfactant, at least one detersive surfactant, water, and an amine functional siloxane polymer. The polymer has the formula

wherein R' denotes an alkyl group of 1 to 4 carbons or a phenyl group, with the proviso that at least 50 percent of the total R' groups are methyl; Q denotes an amine functional substitutent of the formula —R"Z, wherein R" is a divalent alkylene radical of 3 to 6 carbon atoms or a radical of the formula —CH$_2$CH$_2$CH$_2$OCH$_2$—CHOHCH$_2$— and Z is a monovalent radical selected from the group consisting of —NR$_2$''', —NR''''(CH$_2$)$_n$NR$_2$'''; and

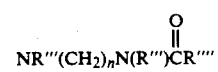

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 3000; y has an average value of 0 to 100 when z is 1, y has an average value of 1 to 100 when z is 0; with the proviso that in all cases y has an average value that is not greater than one tenth the average value of x.

Some particular features of the suspension shampoo of the present invention is that it is free of viscosity modifying thickening compositions. This is advantageous because thickeners tend to negatively effect the combing and feel of hair. The presence of thickeners in shampoo formulations requires additional processing steps in order to homogenize the thickener compositions in the formulation. Thus, pre-mixing and pre-neutralizations sequences are often required in order to formulate such thickener containing shampoos, which is a disadvantage from a processing standpoint. Shampoos containing thickeners also suffer from the disadvantage in that the thickener composition itself may possess functionalities which are incompatible with amine functional siloxanes, with the result that there occurs within the shampoo, such negative effects as precipitation, discoloration, and ammonia gas liberation.

In addition to the amine functional siloxane polymer and water, the shampoo suspension of the present invention contains at least one nonionic surfactant such as a fatty acid alkanolamide surfactant or amine oxide surfactant. The shampoo suspension also contains at least one detersive surfactant such as an anionic surfactant or an amphoteric surfactant. Preferably, the nonionic surfactant is present in the suspension in an amount between 0.1 to ten percent by weight, while the detersive surfactant is present in the suspension in an amount between three to thirty percent by weight. Water constitutes in the suspension an amount between fifty to 96.7 percent by weight, and the amine functional siloxane polymer is present in the suspension in an amount between 0.1 to ten percent by weight.

It is essential to the present invention that the amine functional siloxane polymer be present in the suspension in the form of insoluble particles dispersed in the mixture, and that the particles have a diameter in the suspension of the order of magnitude of between about one micron to about one hundred microns. It has been determined that the particles should have an average diameter in the suspension of about ten microns.

Another particular feature of the shampoo suspension of the present invention is that the amine functional siloxane polymer in the suspension should preferably have a mole percent of amine units of the order of magnitude of about 0.05 to about 1.5. Most preferably, the mole percent of amine units should be from 0.05 to 0.8. In addition, it is preferred that the shampoo suspension contain an amine functional siloxane polymer having a viscosity of from about one thousand Centistokes to about 13,000 Centistokes, or higher, measured at twenty-five degrees Centigrade.

These and other features, objects, and advantages, of the herein defined present invention will become more apparent when considered in conjunction with the following detailed description thereof.

DETAILED DESCRIPTION OF THE INVENTION

For purposes of the present invention, the term "suspension" is used to define a mixture constituting a plurality of individual components, the mixture containing insoluble particles of an amine functional siloxane polymer, the particles being uniformly dispersed and distributed throughout a liquid medium, and the particles having a diameter in the suspension mixture of the order of magnitude of from about one micron to about one hundred microns. Thus, a suspension is distinct from a solution which may include soluble particles of a diameter less than the wavelength of visible light, or of the order of magnitude of about 0.03-0.04 microns and less. A suspension is also distinct from either a microemulsion or an emulsion which permit, respectively, particles sizes of the order of magnitude of 0.06 microns or less, and 0.1-0.6 microns. In contrast to a solution, the particles in a suspension can therefore vary anywhere from about two hundred-fifty times larger than the particles in a solution, to for instance upwards of one thousand times larger. Thus, an obvious difference is seen to exist between solution and suspension technologies.

As noted hereinabove, the suspension shampoo composition of this invention includes four ingredients. These ingredients are water, a nonionic surfactant, a detersive surfactant, and the amine functional siloxane polymer. The amine functional siloxane polymer may be blended with dimethylcyclosiloxanes without adversely effecting the composition. A detailed list of suitable nonionic and detersive surfactants suitable for use in accordance with the present invention can be found in U.S. Pat. No. 4,559,227, issued Dec. 17, 1985, which has been incorporated herein by reference as previously stated. The generic details of the amine functional siloxane polymer can also be found in the '227 patent, as to the general structure of the polymer and general methods of its preparation. In addition, the processing steps in the formulation of the shampoos of the present invention, and the test procedures for the determination of the suitability of the shampoos of the present invention are generally similar to those detailed in the '227 patent, and reference can be had thereto if required.

The following examples are set forth in order to illustrate the concept of the present invention.

EXAMPLE I

Into a vessel was placed a mixture containing 2,479.5 grams of dimethylsiloxane units; 7.3 grams of methyl-(aminoethylaminoisobutyl) siloxane units; 13.0 grams of the compound $(CH_3)_3SiOSi(CH_3)_2OSi(CH_3)_2OSi(CH_3)_3$; and 0.36 grams of potassium hydroxide pellets. The mixture was heated over a five hour period at one hundred-fifty degrees Centigrade. The mixture was cooled and treated with 0.58 grams of glacial acetic acid in order to neutralize the potassium silanolate catalyst. Twelve hundred grams of dimethylsiloxane units were added to the mixture. The material in the vessel was filtered in order to obtain a fluid product having a viscosity measured at twenty-five degrees Centigrade of 1,654.4 centistokes.

EXAMPLE II

Into a vessel was placed a mixture containing 2,479.5 grams of dimethylsiloxane units; 7.3 grams of methyl-(aminoethylaminoisobutyl) siloxane units; 13.0 grams of the compound $(CH_3)_3SiOSi(CH_3)_2OSi(CH_3)_2OSi(CH_3)_3$; and 0.36 grams of potassium hydroxide pellets. The mixture was heated over a five hour period at one hundred-fifty degrees Centigrade. The mixture was cooled and treated with 0.58 grams of glacial acetic acid in order to neutralize the potassium silanolate catalyst. Four hundred grams of dimethylsiloxane units were added to the mixture. The material in the vessel was filtered in order to obtain a fluid product having a viscosity measured at twenty-five degrees Centigrade of 5,743 centistokes.

EXAMPLE III

Into a vessel was placed a mixture containing 485 grams of dimethylsiloxane units; 8.15 grams of methyl-(aminoethylaminoisobutyl) siloxane units; 6.85 grams of the compound $(CH_3)_3SiOSi(CH_3)_2OSi(CH_3)_2OSi(CH_3)_3$; and 2.8 grams of $(2.05 \times 10^{-3}$ mols $K^+$, 0.038 mols dimethylsiloxane units) potassium silanolate. The mixture was heated over a five hour period at one hundred-fifty degrees Centigrade. The mixture was cooled and treated with 0.17 grams of glacial acetic acid in order to neutralize the potassium silanolate catalyst. The material in the vessel was filtered in order to obtain a fluid product having a viscosity measured at twenty-five degrees Centigrade of 1,093 centistokes. The amine neutral equivalent of the product was 5,170.

EXAMPLE IV

Into a vessel was placed a mixture containing 977.9 grams of dimethylsiloxane units; 8.2 grams of methyl-(aminoethylaminoisobutyl) siloxane units; 13.9 grams of the compound $(CH_3)_3SiOSi(CH_3)_2OSi(CH_3)_2OSi(CH_3)_3$; and 0.2 grams of potassium hydroxide pellets. The mixture was heated over a five hour period at one hundred-fifty degrees Centigrade. The mixture was cooled and treated with 0.4 grams of glacial acetic acid in order to neutralize the potassium silanolate catalyst. The material in the vessel was filtered in order to obtain a fluid product having a viscosity measured at twenty-five degrees Centigrade of 1,110 centistokes.

EXAMPLE V

A shampoo suspension in accordance with the present invention was prepared by the following procedure. One part of the amine functional siloxane polymer fluid of Example III, and two parts of the nonionic surfactant cocamide DEA (the coco acid amide of diethanolamine), were combined in a vessel and manually stirred until an opaque homogeneous blend of the ingredients was obtained. The blend was added accompanied by stirring to fifty parts of a detersive surfactant solution which contained fifteen parts of sodium lauryl ether-2 sulfate and thirty-five parts of water. An additional 45.5 parts of water was added. The pH of the mixture was adjusted to six with a twenty-five percent aqueous citric acid solution. Ammonium chloride in the amount of 1.5 parts was added. The ingredients in the vessel were mixed together to form a hazy homogeneous suspension containing particles of the amine functional siloxane polymer. The particles of the amine functional siloxane polymer were of a diameter within the range of about three to fifty microns. The shampoo suspension had a viscosity of about four thousand centistokes measured at twenty-five degrees Centigrade. Testing of this suspension shampoo formulation is explained below and shown in Table I.

A panel test was used to generate hair combing and feel data in order to illustrate the effectiveness of the shampoo suspensions of the present invention. Results of the panel test are shown in Table I. The panelist were requested to evaluate European hair tresses on the basis of feel and the ease of wet and dry combing. The scale ranged from one to five, with one being easy to comb with very little or no resistance or of the best feel, and five being impossible to get the comb through the hair tress or of an unacceptable feel. The suspension shampoo formulations were applied to wet hair tresses after the tresses had been shampooed with one-half gram of the suspension, an amount of the suspension shampoo formulation sufficient to thoroughly coat the hair. The shampoo suspensions were allowed to remain on the hair for two minutes and then were rinsed from the hair tresses with warm water. Following evaluation by the panelists of the wet combing of the hair tresses, the tresses were blown dry and then evaluated by the panelists for dry combing and dry feel. Details of the pretreatment of the hair tresses is set forth in the '227 patent.

EXAMPLE VI

Example V was repeated except that the amine functional siloxane polymer prepared in accordance with Example IV was used in the suspension shampoo formulation. The shampoo suspension had a viscosity of 4,500 centistokes measured at twenty-five degrees Centigrade. Test results of the suspension shampoo formulation are shown in Table I.

EXAMPLE VII

Example VI was repeated except that the nonionic surfactant was changed to three parts of lauramide DEA, and the detersive surfactant was changed to thirty parts of an aqueous solution containing fifteen parts of ammonium lauryl sulfate. The shampoo suspension had a viscosity of 4,000 centistokes measured at twenty-five degrees Centigrade. Test results of the suspension shampoo formulation are shown in Table I.

EXAMPLE VIII

Example V was repeated except that the amine functional siloxane polymer prepared in accordance with Example I was used in the suspension shampoo formulation. Test results of the suspension shampoo formulation are shown in Table I.

TABLE I

| SHAMPOO SUSPENSION | WET COMBING | DRY COMBING | DRY FEEL |
|---|---|---|---|
| Example V | 1.5 | 2.0 | 2.75 |
| Control* | 3.75 | 2.5 | 2.75 |
| Example VI | 1.5 | 1.5 | 2.0 |
| Example VII | 1.25 | 2.5 | 1.5 |
| Control* | 3.5 | 3.5 | 3.5 |
| Example VIII | 1.25 | 1.75 | 1.75 |

* = Control included all ingredients except for the amine functional siloxane polymer.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

What is claimed is:

1. A composition comprising a thickener free mixture in the form of a suspension, the suspension including at least one nonionic surfactant, at least one detersive surfactant, water, and an amine functional siloxane polymer having the formula

$$R_{3-z'}Q_zSiO[R_2'SiO]_x[R'QSiO]_ySiQ_zR_{3-z'}$$

wherein R' denotes an alkyl group of 1 to 4 carbons or a phenyl group, with the proviso that at least 50 percent of the total R' groups are methyl; Q denotes an amine functional substitutent of the formula —R"Z, wherein R" is a divalent alkylene radical of 3 to 6 carbon atoms or a radical of the formula —$CH_2CH_2CH_2OCH_2CHOHCH_2$— and Z is a monovalent radical selected from the group consisting of —$NR_2'''$, —$NR'''(CH_2)_nNR_2'''$; and

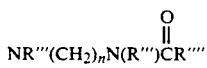

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 3000; y has an average value of 0 to 100 when z is 1, y has an average value of 1 to 100 when z is 0; the amine functional siloxane polymer being present in the suspension in the form of insoluble particles dispersed in the mixture, the particles having a diameter in the suspension of the order of magnitude of about one micron to about one hundred microns, the amine functional siloxane polymer having a mole percent of amine units of the order of magnitude of about 0.05 to about 1.5.

2. The suspension of claim 1 in which the particles have an average diameter in the suspension of about ten microns.

3. The suspension of claim 1 in which the mole percent of amine units is from 0.05 to 0.8.

4. The suspension of claim 1 in which the amine functional siloxane polymer has a viscosity from about one thousand Centistokes to about 13,000 Centistokes measured at twenty-five degrees Centigrade.

5. The suspension of claim 1 in which the nonionic surfactant is selected from the group consisting of fatty acid alkanolamide surfactants and amine oxide surfactants.

6. The suspension of claim 5 in which the detersive surfactant is selected from the group consisting of anionic surfactants and amphoteric surfactants.

7. The suspension of claim 6 in which the nonionic surfactant is present in the suspension in an amount between 0.1 to ten percent by weight.

8. The suspension of claim 7 in which the detersive surfactant is present in the suspension in an amount between three to thirty percent by weight.

9. The suspension of claim 8 in which water is present in the suspension in an amount between fifty to 96.7 percent by weight.

10. The suspension of claim 9 in which the amine functional siloxane polymer is blended with a dimethylcyclosiloxane and is present in the suspension in an amount between 0.1 to ten percent by weight.

* * * * *